United States Patent

Mayer et al.

Patent Number: 6,043,196
Date of Patent: Mar. 28, 2000

[54] HERBICIDAL SULFONYLUREAS, THEIR PREPARATION AND USE

[75] Inventors: Horst Mayer, Ludwigshafen; Gerhard Hamprecht, Weinheim; Karl-Otto Westphalen, Speyer; Matthias Gerber, Limburgerhof; Helmut Walter, Obrigheim, all of Germany

[73] Assignee: BASF Aktiengesellschaft, Ludwigshafen, Germany

[21] Appl. No.: 09/002,836

[22] Filed: Jan. 5, 1998

Related U.S. Application Data

[63] Continuation of application No. 08/433,521, filed as application No. PCT/EP93/03038, Oct. 30, 1993, abandoned.

[30] Foreign Application Priority Data

Nov. 12, 1992 [DE] Germany ............ 42 38 175

[51] Int. Cl.[7] .................... C07D 251/42; A01N 43/66
[52] U.S. Cl. .................................. 504/212; 544/211
[58] Field of Search ................ 544/211; 504/212

[56] References Cited

PUBLICATIONS

DAUS "Intellectual Property Journal" vol. 12, No. 3, Sep. 1998 pp. 333–354.

*Primary Examiner*—John M. Ford
*Attorney, Agent, or Firm*—Keil & Weinkauf

[57] ABSTRACT

Sulfonylureas of the general formula I

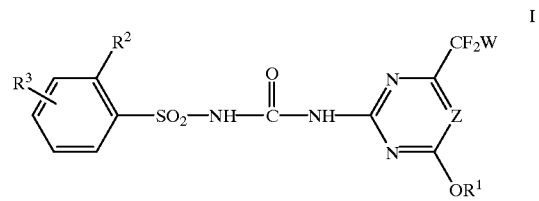

where $R^1$ is a methyl or ethyl group;

$R^2$ is $C_1$–$C_3$-alkoxycarbonyl, a $C_1$–$C_2$-alkyl group which carries 1 to 5 fluorine atoms, methylsulfonyl, dimethylaminosulfonyl, thiomethyl, methylsulfinyl, methylsulfonyloxy, trifluoromethoxy, difluoromethoxy, difluorochloromethoxy, difluorochloromethyl or nitro;

$R^3$ is hydrogen, methyl, methoxy, ethoxy, fluorine, chlorine or thiomethyl;

W is hydrogen or chlorine and

Z is CH or N and their agriculturally utilizable salts are described.

14 Claims, No Drawings

HERBICIDAL SULFONYLUREAS, THEIR PREPARATION AND USE

This is a continuation of prior application Ser. No. 08/433,521, now abandoned, which is a 371 of PCT/EP93/03038 filed Oct. 30, 1993.

The present invention relates to sulfonylureas of the general formula I

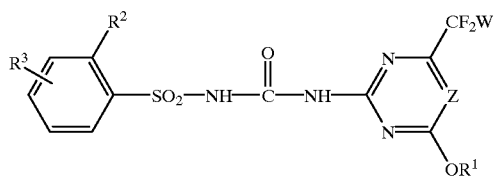

where

R$^1$ is a methyl or ethyl group;

R$^2$ is C$_1$–C$_3$-alkoxycarbonyl, a C$_1$–$_2$-alkyl group which carries 1 to 5 fluorine atoms, methylsulfonyl, dimethylaminosulfonyl, thiomethyl, methylsulfinyl, methylsulfonyloxy, trifluoromethoxy, difluoromethoxy, difluorochloromethoxy, difluorochloromethyl or nitro;

R$^3$ is hydrogen, methyl, methoxy, ethoxy, fluorine, chlorine or thiomethyl;

W is hydrogen or chlorine and

Z is CH or N and their agriculturally utilizable salts.

In U.S. Pat. No. 4,120,691, the nearest structures described are the triazine compound A and the pyrimidine derivative B (cf. also U.S. Pa. No. 4,169,719).

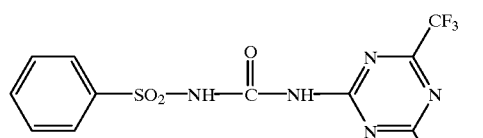

In EP-A 48 808, sulfonylureas D having a substituent in the aromatic moiety are described.

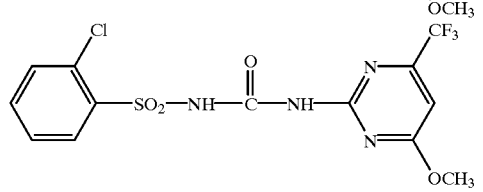

In EP-A 48 143, two N-methylated sulfonylureas E are shown without closer characterization.

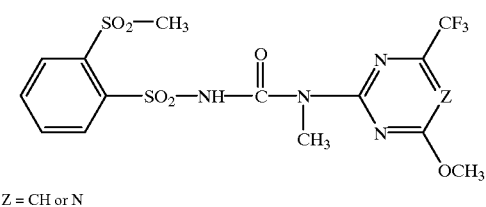

Z = CH or N

EP-A 388 873 covers benzoic acid esters of the structure F.

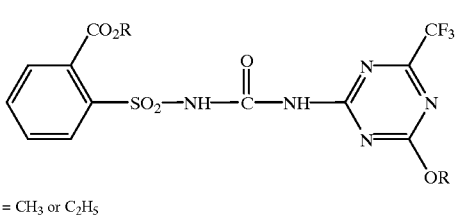

R = CH$_3$ or C$_2$H$_5$

In U.S. Pat. No. 4,310,346, sulfonamides of the type G are listed.

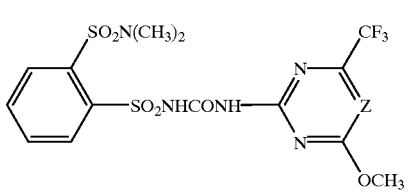

Z = CH or N

German Laid-Open Application DE-OS 40 38 430 (WO 92/09608) describes trifluoromethyl-substituted triazines of type H.

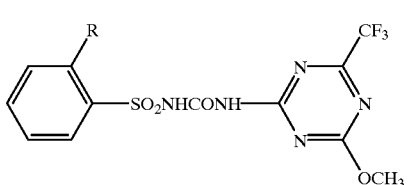

R = halogen, CF$_3$,
alkylsulfonyl or
O(CH$_2$)$_2$OCH$_3$

EP-A 120 814 mentions the compound J without details of physical data.

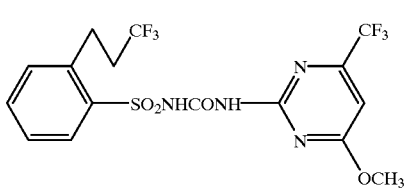

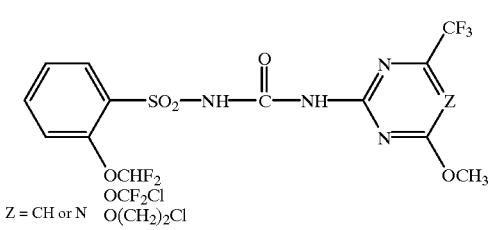

It is an object of the present invention to synthesize sulfonylureas which, compared with the known representatives of this class of herbicide, have improved properties and are particularly distinguished by high selectivity in sensitive crops.

We have now found that this object can be achieved by the sulfonylureas of the formula I defined at the outset.

In the formula I, $C_1$–$C_3$-alkoxycarbonyl is methoxycarbonyl, ethoxycarbonyl, n-propoxycarbonyl or isopropoxycarbonyl and a $C_1$–$C_2$-alkyl group which carries 1 to 5 fluorine atoms is methyl, substituted by 1 to 3 fluorine atoms, or ethyl, substituted by 1 to 5 fluorine atoms, eg. trifluoromethyl, difluoromethyl, 2,2,2-trifluoroethyl or 1,1,2,2-tetrafluoroethyl.

Sulfonylureas of the formula I are particularly preferred in which $R^2$ is methoxycarbonyl, trifluoromethyl, dimethylaminosulfonyl, trifluoromethoxy, difluoromethoxy or methylsulfonyl, and also sulfonylureas having a ttiazine substituent (Z=N). Compounds I with difluoromethyl substitution of hetero atoms (W=H) are additionally particularly important.

The sulfonylureas of the formula I according to the invention are accessible by various routes which are described in the literature. By way of example, particularly advantageous routes (A–C) may be illustrated in greater detail in the following.

dichloronaphthalene, carbon tetrachloride, 1,1,1- or 1,1,2-trifluoroethane, trichloroethylene, pentachloroethane, o-, m- or p-difluorobenzene, 1,2-dichloroethane, 1,1-dichloroethane, 1,2-cis-dichloroethylene, chlorobenzene, fluorobenzene, bromobenzene or iodobenzene, o-, m- or p-dichlorobenzene, o-, p- or m-dibromobenzene, o-, m- or p-chlorotoluene, 1,2,4-trifluorobenzene; ethers, eg. ethyl propyl ether, methyl tert-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole or β,β'-dichlorodiethyl ether, nitrohydrocarbons such as nitromethane, nitroethane, nitrobenzene, o-, m- or p-chloronitrobenzene or o-n-trotoluene; nitriles such as acetonitrile, butyronitrile, isobutyronitrile, benzonitrile or m-chlorobenzonitrile; aliphatic or cycloaliphatic hydrocarbons, eg. heptane, pinane, nonane, or o-, m- or p-cymene, benzene fractions within a boiling point range from 70 to 190° C., cyclohexane, methylcyclohexane, decalin, petroleum ether, hexane, naphtha, 2,2,4-trimethylpentane, 2,2,3-trimethylpentane, 2,3,3-trimethylpentane or octane; esters, eg. ethyl acetate, ethyl acetoacetate or isobutyl acetate; amides, eg. formamide, methylformamide or dimethylformamide; ketones, eg. acetone or methyl ethyl ketone, and suitable mixtures. The solvent is expediently used in an amount of

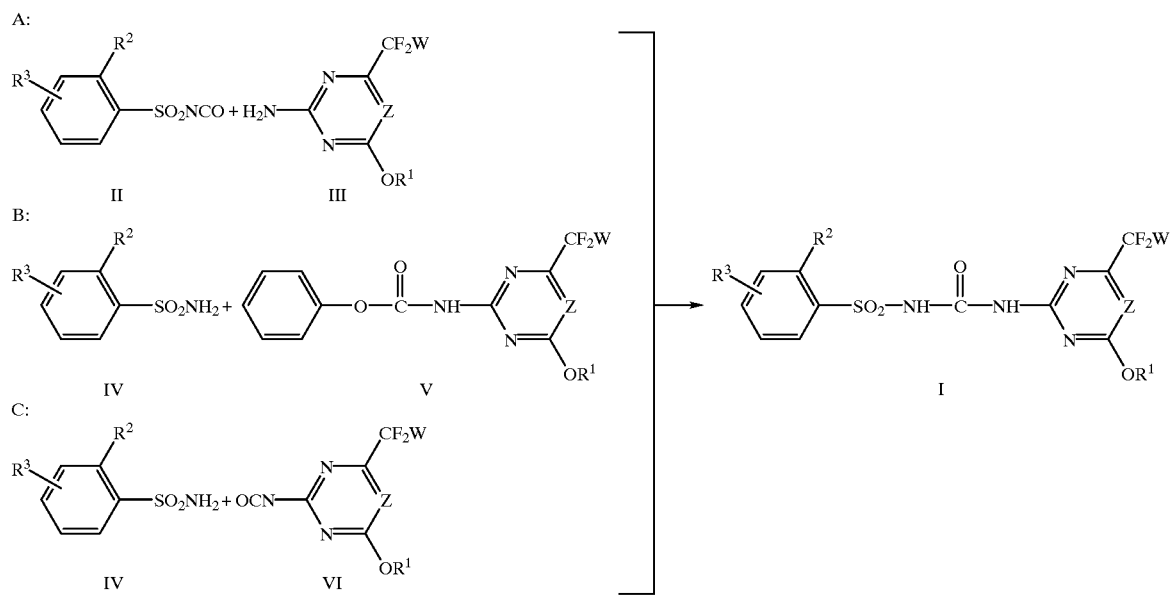

A: A sulfonyl isocyanate II is reacted in a manner known per se (EP-A-162 723) with approximately the stoichiometric amount of a 2-amino-1,3,5-triazine or 2-aminopyrimidine derivative III at from 9 to 120° C., preferably from 10 to 100° C. The reaction can be carried out continuously under normal pressure or under pressure (up to 50 bar), preferably at from 1 to 5 bar.

Inert solvents and diluents are expediently used for the reactions under the respective reaction conditions. Suitable solvents are, for example, halohydrocarbons, in particular chlorohydrocarbons, eg. tetrachloroethylene, 1,1,1,2- or 1,1,2,2-tetrachloroethane, dichloropropane, methylene chloride, dichlorobutane, chloroform, chloronaphthalene, from 100 to 2000% by weight, preferably from 200 to 700% by weight, based on the starting substance II.

The compound II required for the reaction is in general employed in approximately equimolar amounts (using an excess or deficit of eg. 0 to 20%, based on the respective starting substance III). The starting substance III can be introduced in one of the diluents mentioned and the starting substance II then added.

The process for preparing the novel compounds is expediently carried out, however, such that the starting substance II is introduced, if appropriate in one of the abovementioned diluents, and the starting substance III is then added.

To complete the reaction, the mixture is subsequently stirred after the addition of the components for a further 20 minutes to 24 hours at from 0 to 120° C., preferably from 10 to 100° C.

A reaction accelerator which can be used is advantageously a tertiary amine, eg. pyridine, α, β or γ-picoline, 2,4- or 2,6-lutidine, 2,4,6-collidine, p-dimethylaminopyridine, trimethylamine, triethylamine, tri(n-propyl)amine, 1,4-diaza[2.2.2]bicyclooctane [DABCO] or 1,8-diazabicyclo[5.4.0]undec-7-ene in an amount of from 0.01 to 1 mol per mole of starting substance II.

The final substance I is isolated from the reaction mixture in a customary manner, eg. by removal of solvent by distillation or directly by filtering off with suction. The residue which remains can additionally be washed with water or dilute acid to remove basic impurities. However, the residue can also be dissolved in a water-immiscible solvent and washed as described. The desired final substances are obtained here in pure form. If necessary they can be purified by recrystallization, stirring in an organic solvent which takes up the impurities or chromatography.

Preferably, this reaction is carried out in acetonitrile, methyl tert-butyl ether, toluene or methylene chloride in the presence of from 0 to 100 mol equivalents, preferably from 0 to 50 mol equivalents, of a tertiary amine such as 1,4-diazabicyclo[2.2.2]octane or triethylamine.

B: A sulfonamide of the formula IV is reacted in a manner known per se (EP-A 141 777 or EP-A 101 670) in an inert organic solvent with approximately the stoichiometric amount of a phenyl carbamate V and from 0 to 120° C., preferably from 20 to 100° C. The reaction can be carried out continuously or batchwise at normal pressure or under pressure (up to 50 bar), preferably at from 1 to 5 bar.

Bases such as tertiary amines can be added here which accelerate the reaction and improve the product quality. Suitable bases for this purpose are those indicated under A, in particular triethylamine, 2,4,6-collidine, 1,4-diazabicyclo[2.2.2]octane [DABCO] or 1,8-diazabicyclo[5.4.0]undec-7-ene (DBU), in an amount of from 0.01 to 1 mol per mole of starting substance IV.

The solvents or diluents expediently used are those indicated under A.

The solvent is used in an amount of from 100 to 2000% by weight, preferably from 200 to 700% by weight, based on the starting material IV.

The compound IV required for the reaction is in general employed in approximately equimolar amounts (using an excess or deficit of eg. from 0 to 20%, based on the respective starting substances V). The starting substance V can be introduced into one of the abovementioned diluents and the starting substance IV then added.

However, the starting substance IV can also be introduced into one of the solvents mentioned and the carbamate V then added. In both cases one of the bases mentioned can be added as a catalyst before or during the reaction.

To complete the reaction, the mixture is subsequently stirred after the addition of the components for a further 20 minutes to 24 hours at from 0 to 120° C., preferably from 10 to 100° C., in particular from 20 to 80° C.

The sulfonylureas of the formula I are isolated from the reaction mixture using the customary methods, such as described under A.

C: A sulfonamide of the formula IV is reacted in a manner known per se (EP-A 234 352) in an inert organic solvent with approximately the stoichiometric amount of an isocyanate VI at from 0 to 150° C., preferably from 10 to 100° C. The reaction can be carried out continuously or batchwise at normal pressure or under pressure (up to 50 bar), preferably at from 1 to 5 bar.

Before or during the reaction, bases such as tertiary amines can be added here which accelerate the reaction and improve the product quality. Suitable bases for this purpose are those indicated under A, in particular triethylamine or 2,4,6-collidine, in an amount of from 0.01 to 1 mol per mole of starting substance IV.

The solvents used are expediently those indicated under A. The solvent is employed in an amount of from 100 to 2000% by weight, preferably of 200 to 700% by weight, based on the starting material IV.

The compound IV required for the reaction is in general employed in approximately equimolar amounts (using an excess or deficit of eg. from 0 to 20%, based on the starting materials VI). The starting substance VI can be initially introduced into one of the diluents mentioned and the starting substance IV then added. However, the sulfonamide can also be initially introduced and the isocyanate VI then added.

To complete the reaction, the mixture is stirred after the addition of the components for a further 20 minutes to 24 hours at from 0 to 120° C., preferably from 10 to 100° C., in particular from 20 to 80° C. The final product I can be obtained from the reaction mixture in the customary manner, as described under A:.

The sulfonyl isocyanates of the formula II required as starting substances can be obtained from the corresponding sulfonamides by phosgenation in a manner known per se (Houben-Weyl 11/2 (1985) 1106, U.S. Pat. No. 4,379,769) or by reaction of the sulfonamides with chlorosulfonyl isocyanate (DE-A 31 32 944).

Carbamates of the formula V are accessible by or in a similar manner to known reactions (eg. EP-A 101 670); however, they can also be prepared from the corresponding isocyanates VI by reaction with phenol.

The isocyanates of the formula VI are obtained from the amines of the formula III by treatment with oxalyl chloride or phosgene (in a similar manner to Angew. Chem. 83 (1971) 407, EP-A 388 873).

The sulfonamides can be obtained by reaction of the corresponding sulfonyl chlorides with ammonia (Houben-Weyl, Methoden der organischen Chemie (Methods of organic chemistry), Volume 9 (1955) 605). The sulfonyl chlorides are obtained by Meerwein reaction (diazotization of suitable amines and copper salt-catalyzed sulfochlorination).

2-Amino-4-chlorodifluoromethyl-6-methoxy-1,3,5-triazine and 2-amino-4-difluoromethyl-6-methoxy-1,3,5-triazine can be synthesized as illustrated in the preparation example. The corresponding 6-ethoxy-substituted 1,3,5-triazines can be prepared in a similar manner.

The corresponding pyrimidines of the general formula III are accessible by the following sequence:

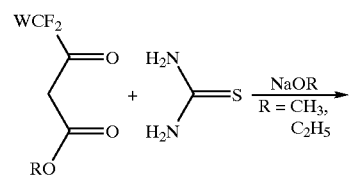

-continued

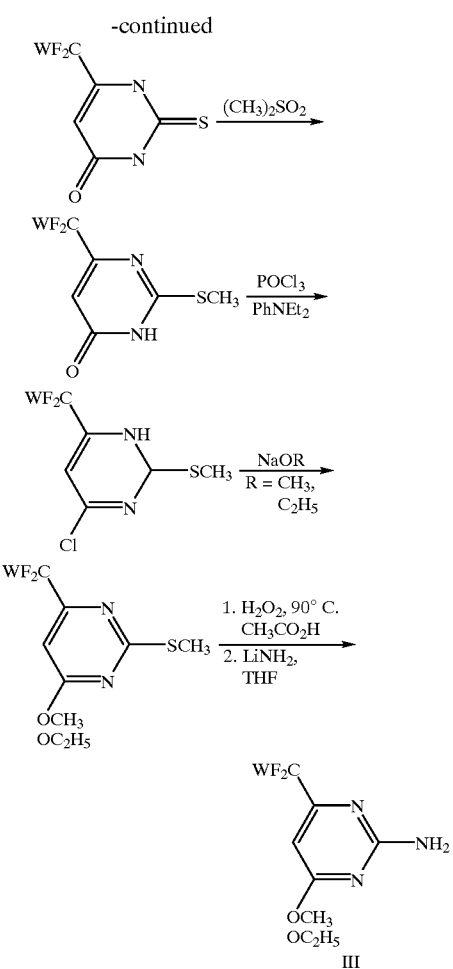

Corresponding reactions are well known (D. J. Brown in "The Chemistry of Heterocyclic Compounds", Interscience Publishers, New York, London, Vol. 14, Heterocycl. Chem. 20 (1983) 219).

The compounds I can be present in the form of their agriculturally utilizable salts, where in general the nature of the salt does not matter. Customarily, the salts of those bases will be suitable which do not adversely affect the herbicidal action of I.

The salts of the compounds I are accessible in a manner known per se (EP-A-304 282, U.S. Pat. No. 4,599,412). They are obtained by deprotonation of the corresponding sulfonylureas I in water or an inert organic solvent at from −80° C. to 120° C., preferably from 0° C. to 60° C., in the presence of a base.

Suitable bases are, for example, alkali metal or alkaline earth metal hydroxides, hydrides, oxides or alkoxides such as sodium, potassium and lithium hydroxide, sodium methoxide, ethoxide and tert-butoxide, sodium and calcium hydride and calcium oxide. Salts of transition metals, preferably manganese, copper, zinc and iron salts and also the ammonium salts which can carry one to three $C_1$–$C_4$-alkyl or hydroxy-$C_1$–$C_4$-alkyl substituents and/or a phenyl or benzyl substituent, preferably diisopropylammonium, tetramethylammonium, tetrabutylammonium, trimethylbenzylammonium and trimethyl(2-hydroxyethyl)ammonium salts, the phosphonium salts, the sulfonium salts, preferably tri-($C_1$–$C_4$)-alkylsulfonium salts, and the sulfoxonium salts, preferably tri-($C_1$–$C_4$)-alkylsulfoxonium salts can also be employed as basic salts.

In addition to water, suitable solvents, for example, are also alcohols such as methanol, ethanol and tert-butanol, ethers such as tetrahydrofuran and dioxane, acetonitrile, dimethylformamide, ketones such as acetone and methyl ethyl ketone and also halogenated hydrocarbons.

Deprotonation can be carried out at normal pressure or at pressures of up to 50 bar, preferably at normal pressure up to an excess pressure of 5 bar.

The compounds I or the herbicidal compositions containing them and their environmentally tolerable salts of alkali metals and alkaline earth metals can very effectively control weeds in crops such as wheat, rice and maize without damaging the crop plants, an effect which occurs especially even at low application rates. They can be applied by spraying, atomizing, dusting, broadcasting or watering in the form of directly sprayable solutions, powders or suspensions, even high-percentage aqueous, oily or other suspensions, or dispersions, emulsions, oil dispersions, pastes, dusting compositions, broadcasting compositions or granules. The application forms depend on the intended use; in each case they should if possible guarantee the finest dispersion of the active compounds according to the invention.

The compounds I are generally suitable for preparing directly sprayable solutions, emulsions, pastes or oil dispersions. Suitable inert additives are, inter alia, mineral oil fractions of medium to high boiling point, such as kerosene or diesel oil, and also coal tar oils and oils of vegetable or animal origin, aliphatic, cyclic and aromatic hydrocarbons, eg. toluene, xylene, paraffin, tetrahydronaphthalene, alkylated naphthalenes or their derivatives, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by addition of water. To prepare emulsions, pastes or oil dispersions, the substrates as such or dissolved in an oil or solvent can be homogenized in water by means of wetting agents, adhesives, dispersants or emulsifiers. However, concentrates consisting of active substance, wetting agent, adhesive, dispersant or emulsifier and possibly solvent or oil can be prepared, which are suitable for dilution with water.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, and of fatty acids, alkyl- and alkylarylsulfonates, alkyl-, lauryl ether and fatty alcohol sulfates, as well as salts of sulfated hexa-, hepta- and octadecanols, and also of fatty alcohol glycol ethers, condensation products of sulfonated naphthaline and its derivatives with formaldehyde, condensation products of naphthalene or of naphthalenesulfonic acids with phenol and formaldehyde, polyoxyethylene octylphenol ether, ethoxylated isooctyl-, octyl- or nonylphenol, alkylphenol or tributylphenyl polyglycol ethers, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the active substances with a solid carrier.

Granules, eg. coated, impregnated and homogeneous granules can be prepared by binding the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegatable products, such as cereal meal, tree bark meal, wood meal and nut shell meal, cellulose powder or other solid carriers.

The formulations in general contain from 0.1 to 95% by weight, preferably from 0.5 to 90% by weight, of active compound. The active compounds are employed here in a purity of from 90 to 100%, preferably from 95 to 100% (according to NMR spectrum).

Examples of such preparations are:

I 20 parts by weight of the compound No. 1.01 are dissolved in a mixture which consists of 80 parts by weight of alkylated benzene, 10 parts by weight of the additional product of from 8 to 10 mol of ethylene oxide to 1 mol of oleic acid N-monoethanolamide and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II 20 parts by weight of the compound No. 1.01 are dissolved in a mixture which consists of 40 parts by weight of cyclohexanone, 30 parts by weight of isobutanol, 20 parts by weight of the additional product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III 20 parts by weight of the active compound No. 1.01 are dissolved in a mixture which consists of 25 parts by weight of cyclohexanone, 65 parts by weight of a mineral oil fraction of boiling point 210 to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV 20 parts by weight of the active compound No. 1.01 are well mixed with 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel and the mixture is ground in a hammer mill. By finely dispersing it in 20,000 parts by weight of water, a spray liquor is obtained which contains 0.1% by weight of the active compound.

V 3 parts by weight of the active compound No. 1.01 are mixed with 97 parts by weight of finely divided kaolin. In this manner, a dusting composition is obtained which contains 3% by weight of the active compound.

VI 20 parts by weight of the active compound No. 1.01 are intimately mixed with 2 parts by weight of calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

The application of the herbicidal compositions or of the active compounds can be carried out pre-emergence or post-emergence. If the active compounds are less tolerable for certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

The application rates of active compound, depending on the target to be controlled, time of year, target plants and stage of growth, are from 0.001 to 1.0, preferably from 0.01 to 0.5, kg/ha of active substance (a.S.).

In consideration of the variety of application methods, the sulfonylureas I or compositions containing them can also be employed in a further number of crop plants for eliminating undesired plants. Suitable crops are, for example, the following:

*Allium cepa, Ananas comosus, Arachis hypogaea, Asparagus officinalis,* Beta vulgaris spp. altissima, Beta vulgaris spp. rapa, *Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spp., *Manihot esculenta, Medicago sativa,* Musa spp., *Nicotiana tabacum* (*N. rustica*), *Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera* and *Zea mays*.

To widen the spectrum of action and to achieve synergistic effects, the substituted sulfonylureas of the formula I can be mixed with numerous representatives of other herbicidal or growth-regulating active compound groups and applied together. For example, suitable mixture components are diazines, 4H-3,1-benzoxazine derivatives, benzothiodiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives, quinolinecarboxylic acid derivatives, phenyloxy- or heteroaryloxyphenylpropionic acids and their salts, esters and amides and others.

It may additionally be useful to apply the compounds of the formula I on their own or together in combination with other herbicides and additionally with other crop protection compositions, for example with compositions for controlling pests or phytoathogenic fungi or bacteria. Also of interest is the miscibility with mineral salt solutions which are employed for eliminating nutritional and trace element deficiencies. Non-phytotoxic oils and oil concentrates can also be added.

Examples of the synthesis of the compounds I are given below.

Preparation of the starting substances
2-Amino-4-chlorodifluoromethyl-6-methoxy-1,3,5-triazine a) 2-Amino-4-chlorodifluoromethyl-6-thiomethyl-1,3,5-triazine A suspension of 18.5 g of N-amidinothiourea (adduct with N-methyl-2-pyrrolidone) (85 mmol) in 90 ml of methanol was treated with 10.7 g of dimethyl sulfate (85 mmol) and stirred at from 30 to 40° C. for 3 h. 25 g of methyl chlorodifluoroacetate (0.17 mol) was added dropwise to this solution at 0° C., followed by 30.6 g of a 30% by weight solution of sodium methoxide in methanol (0.17 mol). The cooling was removed and the mixture was subsequently stirred at 25° C. for 16 h. The solvent was removed at 40° C., the residue was stirred with 400 ml of water, and the product was filtered off with suction and dried at 40° C. in a water-jet vacuum. The crude product (m.p. 118° C.) was employed in Stage b) without purification ($^1$H-NMR spectrum (250 MHz, CDCl$_3$, int. TMS, δ (ppm): 6.74 br (1H); 5.94 br (1H); 2.54 s (3H)).

b) 2-Amino-4-chlorodifluoromethyl-6-methoxy-1,3,5-triazine

A solution of 19 g of crude product (84 mmol) from Stage a) in 100 ml of methanol was treated dropwise at 0° C. with 16.2 g of a 30% strength by weight solution of sodium methoxide in methanol (90 mmol). The cooling was removed and the mixture was subsequently stirred at 25° C. for 16 h. A pH of 6 was set by addition of 4N HCl, the solvent was removed at 40° C. in a water-jet vacuum and the residue was stirred with 400 ml of water. The product was filtered off with suction, washed with water and dried at 40° C. in a water-jet vacuum.

13.9 g of the title compound (79% of theory) were thus obtained of m.p. 130° C. ($^1$H-NMR spectrum (250 MHz, CDCl$_3$, int. TMS, δ (ppm): 6.78 br (1H); 6.08 br (1H); 4.03 s (3H)).

2-Amino-6-difluoromethyl-6-methoxy-1,3,5-triazine a) 2-Amino-4-difluoromethyl-6-trichloromethyl-1,3,5-triazine A solution of 70.1 g of difluoroacetic anhydride (0.4 mol) in 200 ml of diethyl ether was treated in portions with 40.7 g of N-(trichloroacetamidino)guanidine (0.2 mol) at 0° C. The mixture was stirred at from 20 to 25° C. for 3 hours. The volatile fractions were removed at 40° C. in a water-jet vacuum, the residue was partitioned between 400 ml of water and 200 ml of methylene chloride and the methylene chloride phase was carefully neutralized with dilute sodium hydroxide solution (2% strength by weight). After separating off and drying the methylene chloride phase over Na$_2$SO$_4$, the solvent was distilled off at 40° C. in a water-jet vacuum. 39.6 g (0.15 mol) (75% of theory) of a spectroscopically pure crude product were thus obtained, which can thus be employed in the subsequent reaction (Stage b) without purification.

$^1$H-NMR spectrum (270 MHz, d$_6$-DMSO, int. TMS, δ (ppm): 8.80 br (2H); 6.78 tr (1H;J$_{H-F}$ 162 Hz)).

b) 2-Amino-4-difluoromethyl-6-methoxy-1,3,5-triazine

A solution of 22.5 g of crude product (85 mmol) from stage a) in 100 ml of methanol was treated dropwise at 0° C. with 1.6 g of a 30% strength by weight solution of sodium methoxide in methanol (9 mmol). The cooling was removed and the mixture was subsequently stirred at 25° C. for 16 hours. After addition of a further 1.6 g of a 30% strength by weight solution of sodium methoxide in methanol (9 mmol), the mixture was subsequently stirred at 25° C. for 3 hours. A pH of 7 was set by addition of 3N hydrochloric acid, the solvent was removed in a water-jet vacuum at 40° C. and the residue was vigorously stirred with 400 ml of water. The product was filtered off with suction, washed with water and dried at 40° C. in a water-jet vacuum.

10.7 g of the title compound (0.61 mol; 71% of theory) were thus obtained. $^1$H-NMR spectrum (270 MHz, d$_6$-DMSO, int. TMS, δ (ppm): 8.02, 7.94 br (2H); 6.55 tr (1H;J$_{H-F}$ 162 Hz); 3.90 s (3H)).

Preparation of the sulfonylureas of the formula I

EXAMPLE 1.03

Methyl [2-[[(4-chlorodifluoromethyl-6-methoxy-1,3,5-triazin-2-yl)-aminocarbonyl]aminosulfonyl]benzoate A solution of 4.2 g of 2-amino-4-chlorodifluoromethyl-6-methoxy-1,3,5-triazine (20 mmol) in 20 ml of methylene chloride was treated at 25° C. with a solution of 4.8 g of 2-methoxycarbonylbenzenesulfonyl isocyanate (20 mmol) in 5 ml of methylene chlor-ide. The mixture was stirred at 25° C. for 16 h, the solvent was removed in a water-jet vacuum at 40° C. and the solid residue was stirred with 100 ml of a hexane/diethyl ether mixture (v:v, 1:1). The separated product was filtered off with suction, washed with a little ether and dried. The title compound (3.2 g, 35% of theory) of m.p. 174 to 175° C. was obtained by recrystallizing from methanol/water.

EXAMPLE 1.05

N-[(4-Chlorodifluoromethyl-6-methoxy-1,3,5-triazin-2-yl)aminocarbonyl]-2-nitrobenzenesulfonamide A solution of 4.2 g of 2-amino-4-chlorodifluoromethyl-6-methoxy-1,3,5-triazine (20 mmol) in 20 ml of methylene chloride was treated at 25° C. with a solution of 4.6 g of 2-nitrobenzenesulfonyl isocyanate (20 mmol) in 5 ml of methylene chloride. The mixture was subsequently stirred at 25° C. for 16 h, and the deposited product was filtered off with suction, washed with a little ether and dried at 40° C. in a water-jet vacuum. 3.1 g of the title compound (35% of theory) of m.p. 181° C. were thus obtained.

EXAMPLE 1.06

Sodium N-[(4-chlorodifluoromethyl-6-methoxy-1,3,5-triazin-2-yl)aminocarbonyl]-2-nitrobenzenesulfonamide A suspension of 1.5 g of N-((4-chlorodifluoromethyl-6-methoxy-1,3,5-triazin-2-yl)aminocarbonyl]-2-nitrobenzenesulfonamide (3.4 mmol) in 10 ml of methanol was treated at 25° C. with 0.62 g of a 30% strength by weight solution of sodium methoxide (3.4 mmol) in methanol, whereupon dissolution occurred. The mixture was subsequently stirred at 25° C. for 30 min and the volatile fractions were removed at 40° C. in a water-jet vacuum. The title compound was thus obtained in quantitative yield with a decomposition point of 169° C.

EXAMPLE 3.01

2-[[(4-Difluoromethyl-6-methoxy-1,3,5-triazin-2-yl) aminocarbonyl]aaminosulfonyl]benzotrifluoride A solution of 2.65 g of 2-amino-4-difluoromethyl-6-methoxy-1,3,5-triazine (15 mmol) in 20 ml of acetonitrile was treated at 25° C. with 3.7 g of 2-trifluoromethylbenzenesulfonyl isocyanate (15 mmol). The mixture was subsequently stirred at 25° C. for 16 h, the solvent was removed in a water-jet vacuum at 40° C. and the solid residue was stirred vigorously with 100 ml of diethyl ether. The product was filtered off with suction, washed with a little ether and dried. 4.3 g (10 mmol, 67% of theory) of the title compound of m.p. 143–145° C. were obtained.

EXAMPLE 3.02

Sodium N-[(4-difluoromethyl-6-methoxy-1,3,5-triazin-2-yl)aminocarbonyl] aminosulfonylbenzotrifluoride A suspension of 1.3 g of 2-[[(4-difluoromethyl-6-methoxy-1,3,5-triazin-2-yl)aminocarbonyl]aminosulfonyl]

benzotrifluoride (3 mmol) in 10 ml of methanol was treated at 25° C. with 0.54 g of a 30% strength by weight solution of sodium methoxide (3 mmol) in methanol, whereupon dissolution occurred. The mixture was subsequently stirred at 25° C. for 30 min and the volatile fractions were removed at 40° C. in a water-jet vacuum. The title compound was thus obtained in quantitative yield with a decomposition point of 189–192° C.

The active compounds mentioned in the following Tables 1 to 4 are obtained by a similar preparative route.

TABLE 1

I

| Active Compound No. | $R^1$ | $R^2$ | $R^3$ | M.p. [° C.] |
|---|---|---|---|---|
| 1.01 | $CH_3$ | $CF_3$ | H | 175–172 |
| 1.02 | $CH_3$ | $CF_3$ | H | 192–193 (d)* |
| 1.03 | $CH_3$ | $CO_2CH_3$ | H | 174–175 |
| 1.04 | $CH_3$ | $CO_2CH_3$ | H | 171 (d)* |
| 1.05 | $CH_3$ | $NO_2$ | H | 181 |
| 1.06 | $CH_3$ | $NO_2$ | H | 169 (d)* |
| 1.07 | $CH_3$ | $SO_2N(CH_3)_2$ | H | 152–154 |
| 1.08 | $CH_3$ | $SO_2N(CH_3)_2$ | H | 125–130 (d)* |
| 1.09 | $CH_3$ | $SCH_3$ | 6-$SCH_3$ | >200 |
| 1.10 | $CH_3$ | $OSO_2CH_3$ | H | |
| 1.11 | $CH_3$ | $OSO_2CH_3$ | H | * |
| 1.12 | $CH_3$ | $OCF_3$ | H | |
| 1.13 | $CH_3$ | $OCH_3$ | H | * |
| 1.14 | $CH_3$ | $OCF_2H$ | H | |
| 1.15 | $CH_3$ | $OCF_2H$ | H | * |
| 1.16 | $CH_3$ | $SO_2CH_3$ | H | |
| 1.17 | $CH_3$ | $SO_2CH_3$ | H | * |
| 1.18 | $CH_3$ | $CO_2C_2H_5$ | H | 159–167 |
| 1.19 | $CH_3$ | $CO_2C_2H_5$ | H | * |
| 1.20 | $CH_3$ | $CO_2iC_3H_7$ | H | |
| 1.21 | $CH_3$ | $CO_2iC_3H_7$ | H | * |
| 1.22 | $CH_3$ | $CO_2CH_3$ | 5-$OCH_3$ | 155–160 |
| 1.23 | $CH_3$ | $CO_2CH_3$ | 5-$OCH_3$ | 165–170 (d)* |

*Na salt

The compounds shown below can also be obtained in a similar manner:

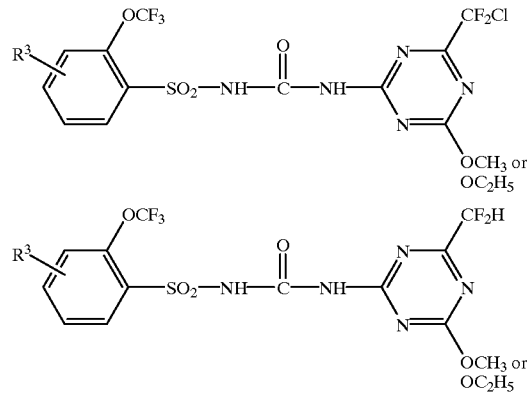

or their Na salts, where $R^3$ has the following meanings:
3-methyl, 5-methyl, 6-methyl, 3-thiomethyl, 5-thiomethyl, 6-thiomethyl, 3-fluoro, 5-fluoro, 6-fluoro, 3-chloro, 5-chloro, 6-chloro, 3-methoxy, 4-methoxy, 5-methoxy, 6-methoxy, 3-ethoxy, 5-ethoxy, 6-ethoxy;

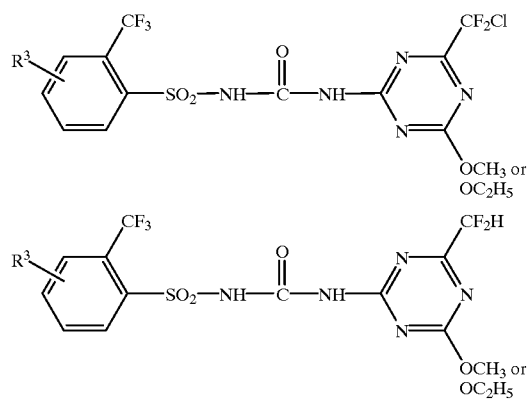

or their Na salts, where $R^3$ has the following meanings:
3-methyl, 5-methyl, 6-methyl, 3-thiomethyl, 5-thiomethyl, 6-thioethyl, 3-fluoro, 5-fluoro, 6-fluoro, 3-chloro, 5-chloro, 6-chloro, 3-methoxy, 4-methoxy, 5-methoxy, 6-methoxy, 3-ethoxy, 5-ethoxy, 6-ethoxy;

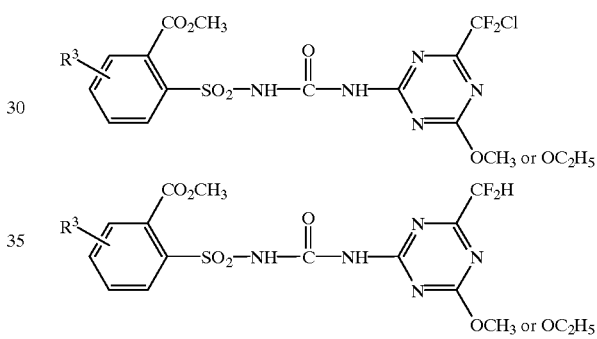

or their Na salts, where $R^3$ has the following meanings:
3-methyl, 5-methyl, 6-methyl, 3-thiomethyl, 5-thiomethyl, 6-thiomethyl, 3-fluoro, 5-fluoro, 6-fluoro, 3-chloro, 5-chloro, 6-chloro, 3-methoxy, 4-methoxy, 5-methoxy, 6-methoxy, 3-ethoxy, 5-ethoxy, 6-ethoxy;

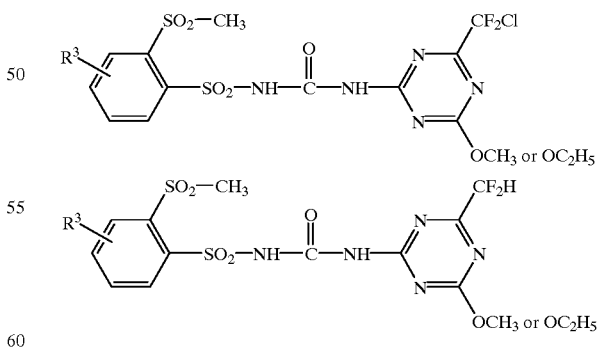

or their Na salts, where $R^3$ has the following meanings:
3-methyl, 5-methyl, 6-methyl, 3-thiomethyl, 5-thiomethyl, 6-thiomethyl, 3-fluoro, 5-fluoro, 6-fluoro, 3-chloro, 5-chloro, 6-chloro, 3-methoxy, 4-methoxy, 5-methoxy, 6-methoxy, 3-ethoxy, 5-ethoxy, 6-ethoxy;

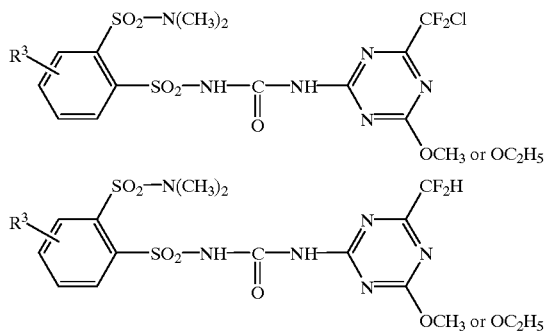

or their Na salts, where $R^3$ has the following meanings:

3-methyl, 5-methyl, 6-methyl, 3-thiomethyl, 5-thiomethyl, 6-thiomethyl, 3-fluoro, 5-fluoro, 6-fluoro, 3-chloro, 5-chloro, 6-chloro, 3-methoxy, 4-methoxy, 5-methoxy, 6-methoxy, 3-ethoxy, 5-ethoxy, 6-ethoxy;

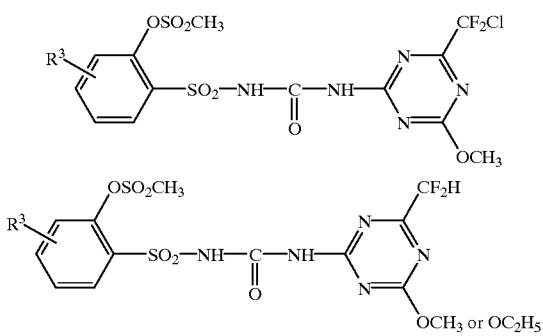

or their Na salts, where $R^3$ has the following meanings:

3-methyl, 5-methyl, 6-methyl, 3-thiomethyl, 5-thiomethyl, 6-thiomethyl, 3-fluoro, 5-fluoro, 6-fluoro, 3-chloro, 5-chloro, 6-chloro, 3-methoxy, 4-methoxy, 5-methoxy, 6-methoxy, 3-ethoxy, 5-ethoxy, 6-ethoxy;

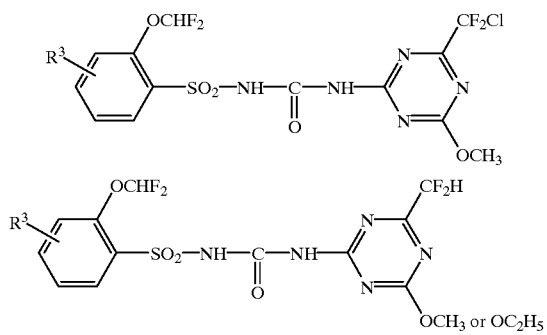

or their Na salts, where $R^3$ has the following meanings:

3-methyl, 5-methyl, 6-methyl, 3-thiomethyl, 5-thiomethyl, 6-thiomethyl, 3-fluoro, 5-fluoro, 6-fluoro, 3-chloro, 5-chloro, 6-chloro, 3-methoxy, 4-methoxy, 5-methoxy, 6-methoxy, 3-ethoxy, 5-ethoxy, 6-ethoxy.

TABLE 2

(Z = CH)

| Active Compound No. | $R^1$ | $R^2$ | $R^3$ | M.p. [° C.] |
|---|---|---|---|---|
| 2.01 | $CH_3$ | $CF_3$ | H | |
| 2.02 | $CH_3$ | $CF_3$ | H | * |
| 2.03 | $CH_3$ | $CO_2CH_3$ | H | |
| 2.04 | $CH_3$ | $CO_2CH_3$ | H | * |
| 2.05 | $CH_3$ | $NO_2$ | H | |
| 2.06 | $CH_3$ | $NO_2$ | H | * |
| 2.07 | $CH_3$ | $SO_2N(CH_3)_2$ | H | |
| 2.08 | $CH_3$ | $SO_2N(CH_3)_2$ | H | * |
| 2.09 | $CH_3$ | $SCH_3$ | 6-$SCH_3$ | |
| 2.10 | $CH_3$ | $OSO_2CH_3$ | H | |
| 2.11 | $CH_3$ | $OSO_2CH_3$ | H | * |
| 2.12 | $CH_3$ | $OCF_3$ | H | |
| 2.13 | $CH_3$ | $OCH_3$ | H | * |
| 2.14 | $CH_3$ | $OCF_2H$ | H | |
| 2.15 | $CH_3$ | $OCF_2H$ | H | * |
| 2.16 | $CH_3$ | $SO_2CH_3$ | H | |
| 2.17 | $CH_3$ | $SO_2CH_3$ | H | * |
| 2.18 | $CH_3$ | $CO_2C_2H_5$ | H | |
| 2.19 | $CH_3$ | $CO_2C_2H_5$ | H | * |
| 2.20 | $CH_3$ | $CO_2iC_3H_7$ | H | |
| 2.21 | $CH_3$ | $CO_2iC_3H_7$ | H | * |

*Na salt

TABLE 3

(Z = N)

| Active Compound No. | $R^1$ | $R^2$ | $R^3$ | M.p. [° C.] |
|---|---|---|---|---|
| 3.01 | $CH_3$ | $CF_3$ | H | 143–145 |
| 3.02 | $CH_3$ | $CF_3$ | H | * 189–192 (d) |
| 3.03 | $CH_3$ | $CO_2CH_3$ | H | 144–146 |
| 3.04 | $CH_3$ | $CO_2CH_3$ | H | * 168 (d) |
| 3.05 | $CH_3$ | $NO_2$ | H | |
| 3.06 | $CH_3$ | $NO_2$ | H | * |
| 3.07 | $CH_3$ | $SO_2N(CH_3)_2$ | H | 160–162 |
| 3.08 | $CH_3$ | $SO_2N(CH_3)_2$ | H | * |
| 3.09 | $CH_3$ | $SCH_3$ | 6-$SCH_3$ | |
| 3.10 | $CH_3$ | $OSO_2CH_3$ | H | 146–148 |
| 3.11 | $CH_3$ | $OSO_2CH_3$ | H | * |
| 3.12 | $CH_3$ | $OCF_3$ | H | 158–161 |
| 3.13 | $CH_3$ | $OCF_3$ | H | * 120 (d) |
| 3.14 | $CH_3$ | $OCF_2H$ | H | 146–148 |
| 3.15 | $CH_3$ | $OCF_2H$ | H | * 161 (d) |
| 3.16 | $CH_3$ | $SO_2CH_3$ | H | |
| 3.17 | $CH_3$ | $SO_2CH_3$ | H | * |
| 3.18 | $CH_3$ | $CO_2C_2H_5$ | H | 167–169 |
| 3.19 | $CH_3$ | $CO_2C_2H_5$ | H | * 158 (d) |
| 3.20 | $CH_3$ | $CO_2iC_3H_7$ | H | |
| 3.21 | $CH_3$ | $CO_2iC_3H_7$ | H | * |

*Na salt

TABLE 4

I (structure shown with R³, R², substituted benzene ring with SO₂—NH—C(O)—NH— linked to pyrimidine ring bearing CF₂H, Z, and OR¹; Z = CH)

| Active Compound No. | R¹ | R² | R³ | M.p. [° C.] |
|---|---|---|---|---|
| 4.01 | CH₃ | CF₃ | H | |
| 4.02 | CH₃ | CF₃ | H | * |
| 4.03 | CH₃ | CO₂CH₃ | H | |
| 4.04 | CH₃ | CO₂CH₃ | H | * |
| 4.05 | CH₃ | NO₂ | H | |
| 4.06 | CH₃ | NO₂ | H | * |
| 4.07 | CH₃ | SO₂N(CH₃)₂ | H | |
| 4.08 | CH₃ | SO₂N(CH₃)₂ | H | * |
| 4.09 | CH₃ | SCH₃ | 6-SCH₃ | |
| 4.10 | CH₃ | OSO₂CH₃ | H | |
| 4.11 | CH₃ | OSO₂CH₃ | H | * |
| 4.12 | CH₃ | OCF₃ | H | |
| 4.13 | CH₃ | OCH₃ | H | * |
| 4.14 | CH₃ | OCF₂H | H | |
| 4.15 | CH₃ | OCF₂H | H | * |
| 4.16 | CH₃ | SO₂CH₃ | H | |
| 4.17 | CH₃ | SO₂CH₃ | H | * |
| 4.18 | CH₃ | CO₂C₂H₅ | H | |
| 4.19 | CH₃ | CO₂C₂H₅ | H | * |
| 4.20 | CH₃ | CO₂iC₃H₇ | H | |
| 4.21 | CH₃ | CO₂iC₃H₇ | H | * |

*Na salt

Use Examples

The herbicidal action of the sulfonylureas of the formula I on the growth of the test plants is shown by the following greenhouse tests.

The cultivation containers used were plastic flowerpots containing loamy sand with about 3.0% humus as a substrate. The seeds of the test plants were sown separately according to species.

In the case of pre-emergence treatment, the active compounds suspended or emulsified in water were applied directly after sowing by means of finely dispersing nozzles. The containers were lightly watered in order to promote germination and growth and then covered with transparent plastic hoods until the plants had taken root. This covering causes a uniform germination of the test plants if this has not been adversely affected by the active compounds.

For the purpose of post-emergence treatment, the test plants were first raised, depending on growth form, to a growth height of from 4 to 15 cm and only then treated with the active compounds suspended or emulsified in water. To do this, the test plants were either directly sown and raised in the same containers or they were first raised separately as seed plants and transplanted into the test containers a few days before the treatment. The application rate for post-emergence treatment was 0.06 kg/ha of a.s. (active substance).

The plants were kept in a species-specific manner at 10–25° C. or 20–35° C. The test period extended over 2 to 4 weeks. During this time the plants were tended and their reaction to the individual treatments was assessed.

Assessment was carried out on a scale of from 0 to 100. 100 here means no germination of the plants or complete destruction of at least the above-ground parts and 0 means no damage or normal course of growth.

The plants used in the greenhouse tests were composed of the following species:

| Botanical Name | Common Name |
|---|---|
| Abutilon theophrasti | Velvetleaf |
| Sinapis alba | White mustard |
| Zea mays | Maize |

Using 0.06 kg/ha of a.s. post-emergence, broad-leaved undesired plants can be very well controlled with Example 1.03, together with simultaneous outstanding selectivity in the exemplary crop plant maize.

In the following tables, results of biological investigations are compiled in which the active compound according to the invention Example 1.03 was compared with the compound B known from U.S. Pat. No. 4,169,719 and the active compound according to the invention No. 3.01 was compared with the comparison compound H known from WO 92/09608.

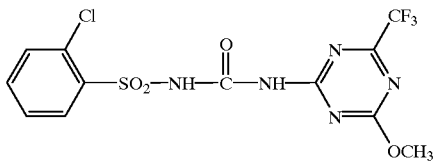

B

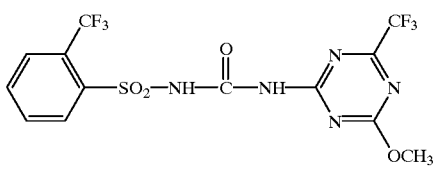

H

TABLE I

Comparison of the herbicidal activity of the exemplary compound No. 1.03 with the known comparison compound B on post-emergence application of 0.0313 or 0.0156 kg/ha of a.s. respectively in the greenhouse.

| | Damage [%] Application rate [kg/ha of a.s.] | | | |
|---|---|---|---|---|
| | Example 2.03 | | B | |
| Test plants | 0.0313 | 0.0156 | 0.0313 | 0.0156 |
| Amaranthus retroflexus | 100 | 100 | 75 | 70 |
| Galium aparine | 95 | 75 | 85 | 40 |
| Polygonum persicaria | 80 | 80 | 40 | 40 |
| Sinapis alba | 90 | 90 | 75 | 75 |
| Solanum nigrum | 90 | 90 | 60 | 60 |
| Veronica spp. | 85 | 75 | 50 | 40 |

TABLE II

Comparison of the herbicidal activity of the exemplary compound No. 3.01 with the known comparison compound H on post-emergence application of 0.063 or 0.0313 kg/ha of a.s. respectively in the greenhouse.

| | Damage [%] Application rate [kg/ha of a.S.] | | | |
|---|---|---|---|---|
| | Example 3.01 | | H | |
| Test plants | 0.063 | 0.0313 | 0.063 | 0.0313 |
| Alopecurus myosuroides | 98 | 98 | 40 | 0 |
| Galium aparine | 95 | 95 | 95 | 95 |
| Ipomea spp. | 98 | 90 | 80 | 80 |
| Sinapis alba | 98 | 98 | 100 | 100 |
| Triticum aestivum | 0 | 0 | 0 | 0 |

We claim:

1. A compound of the general formula I

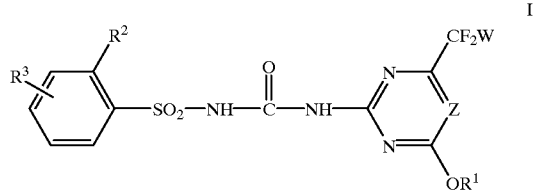

where $R^1$ is a methyl or ethyl group;

$R^2$ is $C_1$–$C_3$-alkoxycarbonyl, a $C_1$–$C_2$-alkyl group which carries 1 to 5 fluorine atoms, methylsulfonyl, dimethylaminosulfonyl, thiomethyl, methylsulfinyl, methyl sulfonyloxy, trifluoromethoxy, difluoromethoxy, difluorochloromethoxy, difluorochloromethyl or nitro;

$R^3$ is hydrogen, methyl, methoxy, ethoxy, fluorine, chlorine or thiomethyl;

W is hydrogen or chlorine and

Z is N and the agriculturally utilizable salts.

2. A compound of the formula I as claimed in claim 1, where $R^2$ is methoxycarbonyl, trifluoromethyl, dimethylaminosulfonyl, trifluoromethoxy, difluoromethoxy or methylsulfonyl.

3. A compound of the formula I as claimed in claim 1, where W is hydrogen.

4. A herbicidal composition containing a compound of the formula I as claimed in claim 1 or its salt and carriers customary for this purpose.

5. A method for controlling undesired plant growth, which comprises allowing a herbicidally active amount of a compound method of the formula I as claimed in claim 1 or of one of its salts to act on the plants and/or their environment.

6. The compound of formula I as defined in claim 1 wherein $R^1$ is methyl.

7. The compound of formula I as defined in claim 1 wherein W is chlorine.

8. The compound of formula I as defined in claim 1 wherein $R^2$ is trifluoromethyl.

9. The compound of formula I as defined in claim 1 wherein $R^2$ is difluoromethoxy.

10. The compound of formula I as defined in claim 1 wherein $R^3$ is hydrogen.

11. The compound of formula I as defined in claim 1 wherein $R^1$ is $CH_3$; $R^2$ is $CF_3$; $R^3$ is H; and W is Cl.

12. The compound of formula I as defined in claim 1 wherein $R^1$ is $CH_3$; $R^2$ is $CO_2CH_3$; $R^3$ is H; and W is Cl.

13. The compound of formula I as defined in claim 1 wherein $R^1$ is $CH_3$; $R^2$ is $CF_3$; $R^3$ is H; and W is H.

14. The compound of formula I as defined in claim 1 wherein $R^1$ is $CH_3$; $R^2$ is $OCF_2H$; $R^3$ is H; and W is H.

* * * * *

UNITED STATES PATENT AND TRADEMARK OFFICE
CERTIFICATE OF CORRECTION

PATENT NO. : 6,043,196
DATED : March 28, 2000
INVENTOR(S) : MAYER et al.

It is certified that error appears in the above-identified patent and that said Letters Patent is hereby corrected as shown below:

IN THE CLAIMS

Column 19, claim 1, line 35, change "thiomethyl, methylsulfinyl" to -- methylthio, methylsufoxide--.

Column 19, claim 1, line 37, change "difluorochiofomethoxy" to-- difluorochloromethoxy--.

Column 19, claim 1, line 38, change " chioromethyl" to --chloromethyl--.

Column 20, claim 1, line 2, change "thiomethyl" to -- methylthio--.

Column 20, claim 5, line 15, after "which" insert -- method--.

Column 20, claim 5, line 17, delete "method"

Signed and Sealed this

Twentieth Day of February, 2001

Attest:

NICHOLAS P. GODICI

Attesting Officer

Acting Director of the United States Patent and Trademark Office